US00PP12763P2

(12) United States Plant Patent
de Jong

(10) Patent No.: US PP12,763 P2
(45) Date of Patent: Jul. 9, 2002

(54) BOUVARDIA PLANT NAMED 'ROYAL DAPHNE'

(76) Inventor: John M. F. de Jong, Floraweg 67, 2371 AM Roelofarendsveen (NL)

( * ) Notice: Subject to any disclaimer, the term of this patent is extended or adjusted under 35 U.S.C. 154(b) by 0 days.

(21) Appl. No.: 09/419,914

(22) Filed: Oct. 12, 1999

(51) Int. Cl.[7] ..... A01H 5/00
(52) U.S. Cl. ..... Plt./352
(58) Field of Search ..... Plt./352

(56) References Cited

FOREIGN PATENT DOCUMENTS

NL PBR BUV0060 3/2001

OTHER PUBLICATIONS

GTITM UPOVROM Citation for 'Royal Daphne' as per NL PBR BUV0060; Sep. 9, 1998.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of Bouvardia plant named 'Royal Daphne' characterized by having light red/purple flowers that are dark red/purple at the center, dark-green foliage, short internodes, which makes it suitable for growing as a potplant, and excellent keeping quality.

2 Drawing Sheets

BACKGROUND OF THE INVENTION

The present invention comprises a new and distinct cultivar of Bouvardia plant, botanically known as *Bouvardia salisb*, and hereinafter referred to by the cultivar name 'Royal Daphne'. Bouvardia is native to Mexico and other countries of Cenral America. The genus is named after the French medical doctor Charles Bouvard who lived from 1572 to 1657.

The genus Bouvardia is a member of the family Rubiaceae and mainly contains small shrubs. Generally, the flowers of Bouvardia contain a four-lobed calyx and a long tubular, funnel-shaped, corolla with four spreading lobes. There are two carpels and two stigmas and the fruit is a capsule.

Bouvardia plants are generally propagated by soft tip cuttings. For example, mother plants are pruned under temperature conditions which prevent flower bud formation (20–22° C). Young shoots with at least two well-developed leaf pairs are rooted.

'Royal Daphne' is a product of a planned breeding program which had the objective of creating new Bouvardia cultivars having improved quality and flowers of various colors. 'Royal Daphne' originated from a hybridization made by the inventor in a controlled breeding program in Roelofarendsveen, the Netherlands, in 1997. The female parent was a proprietary Bouvardia selection designated 95.359.1. The male parent was a proprietary Bouvardia selection designated 95.613.2. 'Royal Daphne' was discovered and selected as one flowering plant within the progeny of the stated cross by the inventor, John M. F. de Jong, in a controlled environment in Roelofarendsveen, the Netherlands.

The first act of asexual reproduction of 'Royal Daphne' was accomplished when soft tip cuttings were taken from the originally discovered plant in 1998 in a controlled environment in Roelofarendsveen, the Netherlands by John M. F. de Jong. Horticultural examination of these asexually reproduced plants has demonstrated that the combination of characteristics as herein disclosed for 'Royal Daphne' are firmly fixed and are retained through successive generations of asexual reproduction.

BRIEF DESCRIPTION OF THE INVENTION

The following traits have been repeatedly observed and are determined to be basic characteristics of 'Royal Daphne' which, in combination, distinguish this Bouvardia as a new and distinct cultivar:

1. Light red/purple flowers that are dark red/purple at the center;
2. Dark-green foliage;
3. Short internodes, which makes it suitable for growing as a potplant; and
4. Excellent keeping quality.

The information presented in the table below shows a comparison between the instant plant and the parental cultivars.

| | 'Royal Daphne' | 95.359.1 | 95.613.2 |
|---|---|---|---|
| Flower color | Petalage color: Base of outer surface of tube is RHS 57 D, and inner surface of tube is RHS 69 D. Petals are RHS 62D with a center of RHS 57B and a base of RHS 62C (upper surface); and RHS 57B with a base of RHS 62C (under surface). | Upper side of petals RHS 62 A suffusing to RHS 66 B toward the base of the petal. Lower side of the petal and the outer surface of the tube: RHS 63 C. | Upper side of petals RHS 67 A. Lower side of the petal and the outer surface of the tube: RHS 67 C |

-continued

| | 'Royal Daphne' | 95.359.1 | 95.613.2 |
|---|---|---|---|
| Leaf color (top side) | RHS 147 A | RHS 137 A | RHS 137 B |
| Leaf color (bottom side) | RHS 137 C | RHS 138 A | RHS 147 B |
| Leaf pubescence | No | No | Yes |

'Royal Daphne' has not been observed under all possible environmental conditions. The phenotype of the new cultivar may vary significantly with variations in environment such as temperature, light intensity, and daylength without any change in genotype. The following observations, measurements, and values describe the pot plants at 12 weeks old, and plants for the production of cut flowers at 2–4 years old, as grown in Roelofarendsveen, the Netherlands under conditions which approximate those generally used in commercial practice. Unless otherwise stated, the following observations, measurements, and values apply to both pot plants and plants for the production of cut flowers.

BRIEF DESCRIPTION OF THE DRAWING

The accompanying color photographic illustrations show typical flower and foliage characteristics of 'Royal Daphne', with colors being as true as possible with illustrations of this type.

Sheet 1 is a side view of 'Royal Daphne'.

Sheet 2 is a top view of the claimed cultivar in bloom showing the flower form.

DETAILED BOTANICAL DESCRIPTION

In the following description, color references are made to The Royal Horticultural Society Colour Chart (R.H.S.).

Origin: Seedling from breeding program.

Parentage:

*Male parent.*—Unnamed plant designated 95.613.2.

*Female parent.*—Unnamed plant designated 95.359.1 .

Classification:

*Botanical.*—A species of the genus *Bouvardia salisb.*

*Commercial.*—Bouvardia cv. 'Royal Daphne'.

Plant:

*Form.*—A vigorously growing small shrub with oppositely arranged leaves and flowers in terminal cymes.

*Height.*—Average height of pot plants from the soil to the top of the inflorescence is 30 cm; the average height from the soil to the leaf plane is 27 cm (depending on growth regulators). Average height of plants for production of cut flowers from the soil to the top of the inflorescence is 140 cm; from the soil to the leaf plane is 140 cm.

*Diameter.*—Average diameter of pot plants is 18 cm. Average diameter of plants for production of cut flowers is 20 cm.

*Growth habit.*—Vigorous: average time to produce a flowering pot plant started with cuttings is 12 weeks; average production cycle of plants for the production of cut flowers is 12 weeks.

*Foliage.*—Quantity: Numerous, 10–15 leaves per stem. Length: 7 cm (pot plants); 9.4 cm (plants for production of cut flowers). Width: 4.9 cm (pot plants); 6.5 cm (plants for production of cut flowers). Shape of leaf: Lanceolate. Apex: Pointed. Base: Narrowed to the petiole. Margin: Smooth, entire. Texture: Smooth. Color: Upper side green RHS 147A; under side RHS 137C. Petiole Length: 0.6 cm (pot plants); 0.8 cm (plants for production of cut flowers). Petiole Diameter: 0.15 cm (pot plants); 0.2 cm (plants for production of cut flowers). Petiole Color: Green RHS 143A.

Bud:

*Form.*—Flask-shaped.

*Color.*—Green RHS 145B.

*Size.*—Small, approximately 1.0 cm in diameter and 2.5–3.0 cm in length.

*Peduncle.*—Length: 0.4 cm (pot plants); 0.6 cm (plants for production of cut flowers). Width: 0.1 cm. Color: Green RHS 143C. Texture: Smooth. Form: Erect.

Flower:

*Flowering season.*—Continuously year-round.

*Size.*—Diameter: 2.0–2.5 cm. Depth: 2.5–3.0 cm.

*Inflorescence type.*—Compound cymes.

*Inflorescence number.*—Average 2 (pot plants); average 6 (plants for production of cut flowers).

*Number of flowers per inflorescence.*—Average 38.

*Inflorescence diameter.*—Average 12.5 cm (pot plants); average 16.5 cm (plants for production of cut flowers).

*Inflorescence depth.*—Average 7.5 cm (pot plant); average 10 cm (plants for production of cut flowers).

*Shape.*—Lobed, tubular corolla.

*Petalage.*—Number of Petals: Four. Length: 0.7 cm (pot plants); 0.9 cm (plants for the production of cut flowers). Width: 0.55 cm (pot plants); 0.75 cm (plants for the production of cut flowers). Arrangement: Concentric circle. Shape: Elliptical. Apex: Pointed. Base: Grown together to the tubular corolla. Margin: Smooth, entire. Texture: Smooth. Appearance: Satiny. Color: Tube: Outer surface, base RHS 57D; inner surface RHS 69D. Petals: RHS 62D with a center of RHS 57B and a base of RHS 62C (upper surface); RHS 57B with a base of RHS 62C (under surface).

*Sepals.*—Length: Average 0.6 cm (pot plants); average 0.8 cm (plants for production of cut flowers). Width: Average 0.25 cm (pot plants); average 0.3 cm (plants for production of cut flowers). Number per flower: 4. Shape: Lanceolate. Apex: Pointed. Base: Fused. Margin: Smooth, entire. Color: Upper side green RHS 137A; under side green RHS 138B.

*Persistence.*—Flowers remain on plant eventually becoming dry.

*Main stem or stalk.*—Length: Up to 80.0 cm. Diameter: 0.35 cm (pot plant); 0.5 cm (plants for the production of cut flowers). Color: Green RHS 148B. Aspect: Sturdy and erect. Internode Length: 6.5 cm (pot plants); 9.5 cm (plants for the production of cut flowers).

*Lasting quality of bloom.*—14–20 days as a cut flower; 35 days as a pot plant.

Reproductive organs:

*Stamens.*—Number: Four. Arrangement: Alternate with corolla lobes.

*Anthers.*—Size: Average length 0.2 cm, average width 0.1 cm. Color: Creamy white RHS 19 D.

*Filaments.*—Length: Approximately 2.0 cm. Color: 69D. Pollen: RHS 19 D, quantity per anther varies from 3000 to 6000 grains.

*Pistils.*—Number: One.

*Seeds.*—Number per capsule: Average 18 (pot plant); 23 (plants for the production of cut flowers). Shape: Round. Length: Average 0.18 cm (pot plant); 0.25 cm (plants for the production of cut flowers). Width: Average 0.19 cm (pot plant); 0.25 cm (plants for the production of cut flowers). Color: RHS 202A.

*Fruit.*—Type: Loculicidal capsule, seeds winged. Length: Average 0.5 cm (pot plant); 0.7 cm (plants for the production of cut flowers). Width: Average 0.5 cm (pot plant); 0.7 cm (plants for the production of cut flowers). Diameter: Average 0.5 cm (pot plant); 0.5 cm (plants for the production of cut flowers). Color: RHS 161A.

Other observations:

*Disease/pest resistance/susceptibility.*—Bouvardia 'Royal Daphne' is susceptible to aphids, white fly, *Fusarium oxysporum, Botryotinia fuckeliana,* Pythium, *Myrothecium roridum.*

*Winter hardiness.*—*Bouvardia*'Royal Daphne' cannot survive temperatures below 0° C.

I claim:

1. A new and distinct cultivar of Bouvardia plant named 'Royal Daphne', as illustrated and described herein.

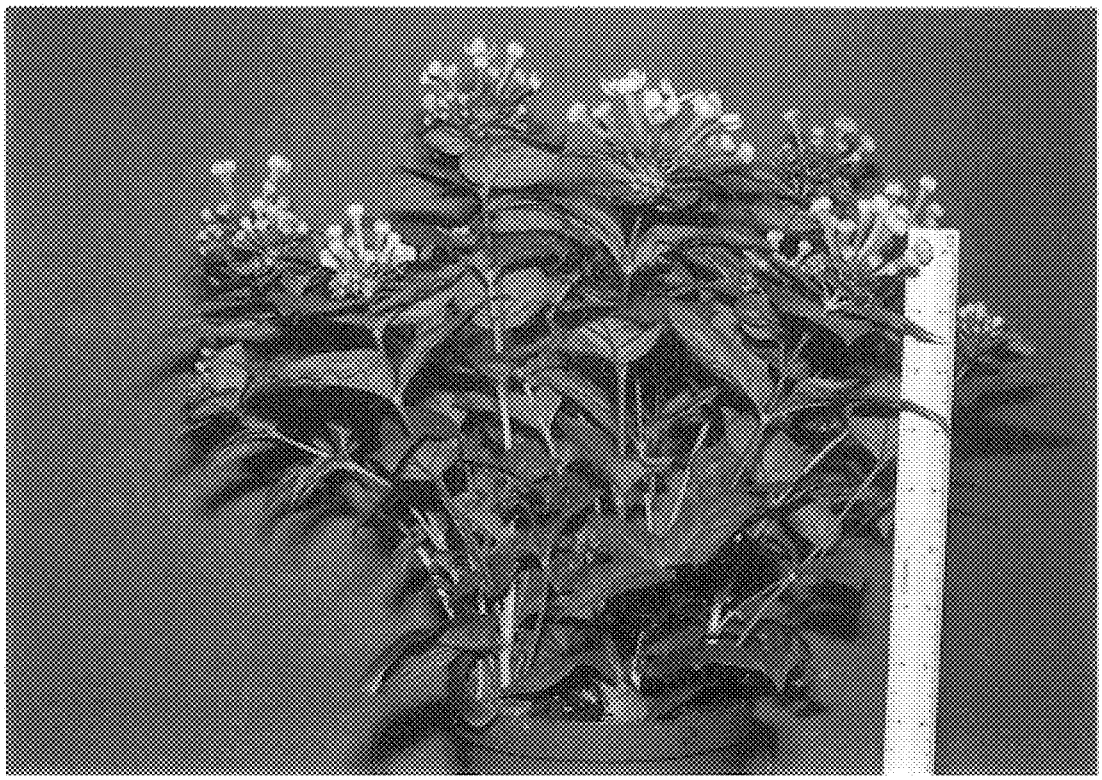

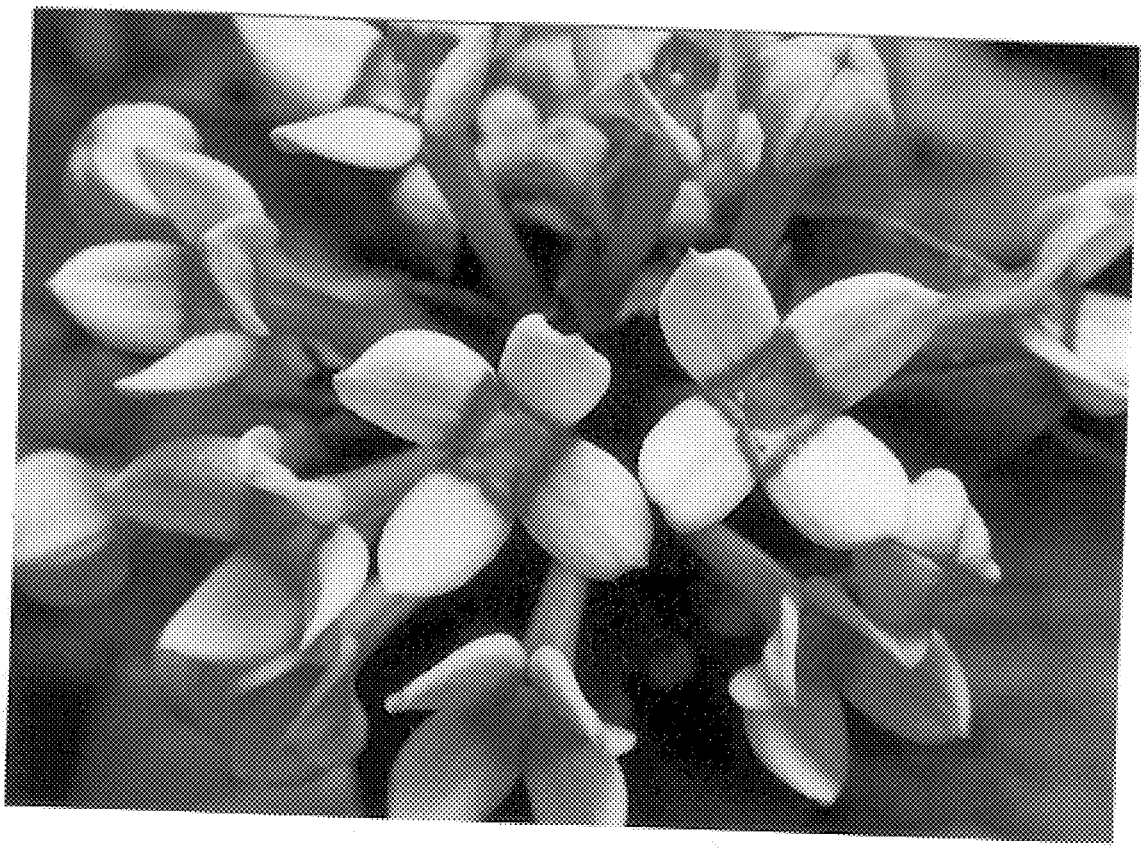

* * * * *